(12) United States Patent
Russell

(10) Patent No.: US 7,258,669 B2
(45) Date of Patent: Aug. 21, 2007

(54) MEDICO-SURGICAL DEVICES

(75) Inventor: Jeremy Colin Russell, Hythe (GB)

(73) Assignee: Smiths Group PLC, London (GB)

( * ) Notice: Subject to any disclaimer, the term of this patent is extended or adjusted under 35 U.S.C. 154(b) by 600 days.

(21) Appl. No.: 10/259,495

(22) Filed: Sep. 30, 2002

(65) Prior Publication Data

US 2003/0065266 A1 Apr. 3, 2003

(30) Foreign Application Priority Data

Oct. 2, 2001 (GB) ................................. 0123596.9

(51) Int. Cl.
*A61B 8/14* (2006.01)
(52) U.S. Cl. ....................... 600/458; 600/439
(58) Field of Classification Search ........ 600/458–471, 600/562, 585, 439, 565; 604/103.01, 264, 604/103.1, 515; 623/1.34, 1.13
See application file for complete search history.

(56) References Cited

U.S. PATENT DOCUMENTS

| | | | | | |
|---|---|---|---|---|---|
| 4,795,439 | A | * | 1/1989 | Guest | 604/43 |
| 4,805,628 | A | * | 2/1989 | Fry et al. | 600/458 |
| 5,054,492 | A | * | 10/1991 | Scribner et al. | 600/463 |
| 5,081,997 | A | * | 1/1992 | Bosley et al. | 600/458 |
| 5,197,482 | A | * | 3/1993 | Rank et al. | 600/562 |
| 5,211,627 | A | * | 5/1993 | William | 604/82 |
| 5,253,653 | A | * | 10/1993 | Daigle et al. | 600/585 |
| 5,259,837 | A | * | 11/1993 | Van Wormer | 604/103.1 |
| 5,562,620 | A | * | 10/1996 | Klein et al. | 604/103.01 |
| 5,771,895 | A | * | 6/1998 | Slager | 600/462 |
| 5,824,042 | A | * | 10/1998 | Lombardi et al. | 623/1.13 |
| 5,832,920 | A | * | 11/1998 | Field | 128/207.14 |
| 5,871,475 | A | * | 2/1999 | Frassica | 604/264 |
| 5,921,933 | A | * | 7/1999 | Sarkis et al. | 600/459 |
| 6,174,330 | B1 | * | 1/2001 | Stinson | 623/1.34 |
| 6,273,858 | B1 | * | 8/2001 | Fox et al. | 600/466 |
| 6,577,904 | B1 | * | 6/2003 | Zhang et al. | 607/116 |
| 6,723,052 | B2 | * | 4/2004 | Mills | 600/459 |
| 2002/0032379 | A1 | * | 3/2002 | Choay et al. | 600/431 |
| 2003/0050531 | A1 | * | 3/2003 | Field | 600/34 |

FOREIGN PATENT DOCUMENTS

| | | |
|---|---|---|
| WO | WO 00/38579 | 7/2000 |
| WO | WO 00/51136 | 8/2000 |

* cited by examiner

*Primary Examiner*—Francis J. Jaworski
(74) *Attorney, Agent, or Firm*—Louis Woo

(57) ABSTRACT

An embryo-transfer catheter has an extruded shaft with a gas-filled lumen that extends helically along the catheter to provide an ultrasound marker. The catheter has a side opening close to a closed rounded patient end. The catheter could be completely transparent to x-rays or the plastics from which it is formed could incorporate an x-ray opaque filler, such as barium sulphate.

11 Claims, 1 Drawing Sheet

MEDICO-SURGICAL DEVICES

BACKGROUND OF THE INVENTION

This invention relates to medico-surgical devices.

The invention is more particularly concerned with medico-surgical devices, such as catheters, that are visible under ultrasound observation.

Ultrasound imaging equipment is increasingly being used during surgical procedures to monitor the location of a device within the body. The visibility of a device under ultrasound depends on various factors including the difference between the acoustic impedance of the material of the device and that of the surrounding medium, such as the patient tissue or body fluid within which the device is located. This difference is relatively low with plastic devices such as catheters making conventional catheters difficult to locate.

Attempts have been made to increase the visibility of medico-surgical devices under ultrasound observation in various ways. The surface of the device may be modified, such as by forming grooves or indentations in its surface. A reflective coating may be applied to the device, such as incorporating bubbles, as described in WO98/19713 and EP0624342. Alternatively, a metal marker may be secured to a plastics catheter.

BRIEF SUMMARY OF THE INVENTION

It is an object of the present invention to provide an alternative medico-surgical device.

According to the present invention there is provided a medico-surgical device comprising a tubular body of a material that provides a relatively low ultrasound reflection during use, the body having a marker that provides a relatively high ultrasound reflection during use, the marker extending on an elongate path along and around the tubular body.

The marker preferably extends along a helical path along the tubular body. The marker may be provided by a gas-filled lumen or by a region of gas-filled bubbles. The tubular body and marker are preferably extruded and the marker may be continuous. The body preferably has a closed rounded patient end and a side opening close to the patient end. The device is preferably an embryo-transfer catheter.

An embryo-transfer catheter according to the present invention, will now be described, by way of example, with reference to the accompanying drawings.

DETAILED DESCRIPTION OF THE PREFERRED EMBODIMENT

Figure 1:
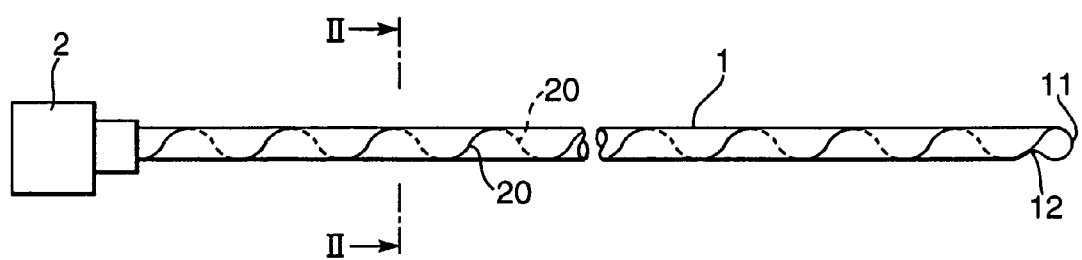
FIG. 1 is a side elevation view of the catheter.
Figure 2:
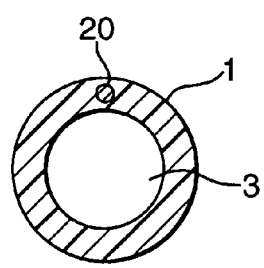
FIG. 2 is a sectional transverse view through the catheter to a larger scale.

The catheter comprises an extruded flexible body or shaft 1 of a clear, transparent polyurethane and a hub 2 of polypropylene joined at the rear end of the shaft. The shaft 1 is between about 180 mm and 380 mm long with a circular section and an outer diameter of 1.6 mm. The shaft has a circular bore 3 with a diameter of 1.1 mm. The forward, right-hand, patient end 11 of the catheter is atraumatically rounded and there is a side opening 12 close to the patient end.

The shaft 1 also has an ultrasound line or marker 20 extruded within its wall. The marker 20 is of an elongate, helical form, extending along the length of the shaft 1 and around its circumference. The path along which the marker extends need not be helical but could be of some other shape that extends along and around the catheter. The marker 20 is selected to reflect a relatively large amount of the ultrasound energy incident on it. This reflectivity may be achieved in various different ways, such as by making the marker a gas-filled lumen or by incorporating gas bubbles into the helical region. Alternatively, the marker may be formed from the same material as the remainder of the shaft with the addition of some other material, such as metal particles. The marker is preferably formed by a rotating extruder head. The marker need not be continuous, it could, for example, be intermittent, providing that it extends along an elongate path along and around the shaft.

The material of the shaft 1 is relatively similar in acoustic properties to the fluid in the uterus and to the fluid medium within the catheter in which the embryo is bathed. For this reason, the shaft 1 itself reflects relatively little of the ultrasound energy from a scanner. The marker 20, however, reflects appreciably more of the ultrasound energy and is, therefore, visible both on the side of the shaft 1 facing the scanner and on the opposite side, that is, through the width of the shaft, when the shaft is filled with a liquid. The marker 20, therefore, appears as a zigzag line extending along the length of the catheter. Passage of a gas bubble, embryo or anything else having different acoustic properties is readily visible on the scanner because it will obscure the marker 20 on the far side of the catheter as it passes along the bore 3. The zigzag configuration of the marker 20 also makes any longitudinal displacement of the catheter considerably more apparent to the clinician than would a straight line marker. The marker of the present invention also has the advantage that it is equally visible regardless of the angular orientation of the catheter. The helical marker can also be used to measure the extent of insertion of the catheter, by counting the number of crests visible.

The catheter could be completely transparent to x-rays or the plastics from which it is formed could incorporate an x-ray opaque filler, such as barium sulphate.

The catheter may be provided as an assembly with an outer sheath (not shown) used to give extra stiffness during insertion.

What I claim is:

1. A catheter for use under external ultrasound observation, the catheter comprising: an open hub at one end by which fluid can be supplied to or from the catheter, said fluid being either a gas or a liquid, a tubular body extending from said hub and opening at an opposite end of said catheter, said tubular body having a wall of a material that provides a relatively low ultrasound reflection during use and through which a fluid passes; and a marker providing a relatively high ultrasound reflection during use, wherein said marker extends helically along said tubular body and along its length so that an interruption in said fluid is readily ascertained by the difference in acoustic properties between said interruption and said fluid, and wherein said marker is extruded within the thickness of the wall as at least one closed gas-filled lumen, such that ultrasound energy is reflected externally of the body by the at least one closed gas-filled lumen.

2. A catheter device according to claim 1, wherein said marker is continuous.

3. A catheter according to claim 1, wherein said body has a closed rounded patient end and a side opening close to the patient end.

4. A catheter according to claim 1, wherein said interruption comprises an embryo.

5. A catheter according to claim 1, wherein said interruption in said fluid in said tubular body obscures said marker on the far side of said tubular body.

6. A catheter according to claim 1, wherein said interruption comprises a gas bubble.

7. A catheter according to claim 1, wherein said marker is configured to be equally visible regardless of the angular orientation of said tubular body relative to a scanner.

8. A catheter according to claim 1, wherein said marker extends intermittently along the entire length of said tubular body.

9. An embryo-transfer catheter for use under external ultrasound observation, the catheter comprising: a hollow tubular body of a plastics material that provides a relatively low ultrasound reflection during use, said body having a closed, rounded patient end and a side opening close to said patient end; and a marker that provides a relatively high ultrasound reflection during use, said marker extending on an elongate path along and around said tubular body within the thickness of the wall of said body, wherein said marker is an extruded at least one closed gas-filled lumen within the wall of the body extending helically along and around said body, such that ultrasound energy is reflected externally of said body by the at least one closed gas-filled lumen and such that an embryo within said catheter is visible.

10. An embryo transfer catheter according to claim 9, wherein said marker extends intermittently along the entire length of said tubular body.

11. An embryo transfer catheter according to claim 9, wherein said marker is continuous.

* * * * *